(12) United States Patent
Marfurt et al.

(10) Patent No.: US 7,867,728 B2
(45) Date of Patent: Jan. 11, 2011

(54) DETERMINING THE CONCENTRATION OF ANALYTES IN SAMPLE BY DIRECT MEDIATION OF ENZYMES

(75) Inventors: Karen L. Marfurt, Edmondsburg, MI (US); Mary Ellen Warchal-Windham, Osceola, IN (US)

(73) Assignee: Bayer HealthCare LLC, Tarrytown, NY (US)

( * ) Notice: Subject to any disclaimer, the term of this patent is extended or adjusted under 35 U.S.C. 154(b) by 880 days.

(21) Appl. No.: 11/660,250

(22) PCT Filed: Aug. 22, 2005

(86) PCT No.: PCT/US2005/029985

§ 371 (c)(1),
(2), (4) Date: Jun. 14, 2007

(87) PCT Pub. No.: WO2006/023927

PCT Pub. Date: Mar. 2, 2006

(65) Prior Publication Data

US 2007/0275430 A1     Nov. 29, 2007

Related U.S. Application Data

(60) Provisional application No. 60/603,881, filed on Aug. 24, 2004.

(51) Int. Cl.
C12Q 1/54     (2006.01)
C12Q 1/26     (2006.01)
C12Q 1/32     (2006.01)
C12M 1/40     (2006.01)
G01N 33/48    (2006.01)

(52) U.S. Cl. .............................. 435/14; 435/25; 435/26; 422/58; 436/95; 436/110; 436/177

(58) Field of Classification Search ........................ None
See application file for complete search history.

(56) References Cited

U.S. PATENT DOCUMENTS

| | | | |
|---|---|---|---|
| 4,211,845 A | 7/1980 | Genshaw et al. | 435/14 |
| 4,390,621 A | 6/1983 | Bauer | 435/14 |
| 4,808,529 A | 2/1989 | Doppelfeld et al. | 435/179 |
| 5,116,729 A | 5/1992 | Ismail et al. | 435/14 |
| 5,126,275 A | 6/1992 | Hatch et al. | 436/169 |
| 5,264,348 A | 11/1993 | Schick et al. | 435/28 |
| 5,290,536 A | 3/1994 | Köcher et al. | 424/7.1 |
| 5,300,637 A | 4/1994 | Hatch et al. | 518/162 |
| 5,322,680 A | 6/1994 | Beck et al. | 428/71 |
| 5,360,595 A | 11/1994 | Bell et al. | 422/56 |
| 5,620,863 A | 4/1997 | Tomasco et al. | 435/14 |
| 5,902,731 A * | 5/1999 | Ouyang et al. | 435/26 |
| 6,103,509 A | 8/2000 | Sode | 435/190 |
| 6,200,773 B1 * | 3/2001 | Ouyang et al. | 435/26 |
| 6,586,199 B2 | 7/2003 | Ouyang et al. | 435/26 |
| 2002/0076751 A1 | 6/2002 | Hattori et al. | 435/69.1 |
| 2003/0077702 A1 | 4/2003 | Shah et al. | 435/69.1 |
| 2003/0094384 A1 | 5/2003 | Vreeke et al. | 205/777.5 |

FOREIGN PATENT DOCUMENTS

| | | |
|---|---|---|
| EP | 0990706 | 4/2000 |
| EP | 1167519 A1 | 2/2002 |
| EP | 1367120 | 12/2003 |
| JP | 11-243949 | 9/1999 |
| JP | 2000171428 A2 | 6/2000 |

OTHER PUBLICATIONS

Written Opinion of the International Searching Authority corresponding to International Patent Application No. PCT/US2005/029985, European Patent Office, dated Jan. 30, 2006, 4 pages.

International Search Report corresponding to International Patent Application No. PCT/US2005/029985, European Patent Office, dated Jan. 30, 2006, 3 pages.

Kuhn, Lance S., "Biosensors: Blockbuster or Bomb? Electrochemical Biosensors for Diabetes Monitoring," The Electrochemical Society Interface, Winter 1998, pp. 26-31.

* cited by examiner

Primary Examiner—Jon P Weber
Assistant Examiner—Kailash C Srivastava
(74) Attorney, Agent, or Firm—Nixon Peabody LLP

(57) ABSTRACT

The glucose content of blood can be determined by contacting a blood sample with a test strip containing a glucose dehydrogenase dependent on PQQ (or derivatives or isomers) thereof as a co-factor, a tetrazolium salt indicator, but in the absence of a mediator.

18 Claims, 2 Drawing Sheets

US 7,867,728 B2

DETERMINING THE CONCENTRATION OF ANALYTES IN SAMPLE BY DIRECT MEDIATION OF ENZYMES

CROSS-REFERENCE TO RELATED APPLICATION

This application is a national-phase application of PCT Application No. PCT/US05/29985, filed Aug. 22, 2005, which claims priority to U.S. Provisional Application No. 60/603,881, filed on Aug. 24, 2004.

FIELD OF THE INVENTION

This invention relates generally to methods for determining the amount of an analyte in biological fluids. More particularly, the invention includes methods for measuring the glucose content of blood or other fluids.

BACKGROUND OF THE INVENTION

The quantitative determination of analytes in biological fluids such as whole blood is of great importance in the diagnosing and treating of certain medical conditions. For example, determining the glucose level in the blood of diabetic individuals, who must frequently check the glucose level in their blood to regulate their diets and medication. Measuring the glucose content of blood can be done by several methods. One method employs an electrochemical biosensor. Another method provides a visual indication of the glucose content such as by developing a color by reaction of an indicator. The present invention is of the later type, although it may have application in electrochemical methods as well.

Electrochemical methods have been described in many patents. They may be divided into several categories including coulometic, amperometric, and cyclic voltammetry. One recent published U.S. patent application is 2003/0094384A1. Japanese published application 2000171428A2 describes the preparation of a glucose electrolytic sensor.

There have been many patents describing methods employing indicators that develop color or other measurable responses when they are chemically oxidized as the last step of a series of reactions. In general, such methods may be broadly divided into those that employ analyte oxidases (e.g., glucose oxidase) that those that employ analyte dehydrogenases (e.g., glucose dehydrogenase). The procedures used are similar, but they employ different enzymes, mediators and indicators.

Methods using glucose oxidase enzymes are taught in many US patents and patent applications. Representative are U.S. Pat. No. 4,211,845; U.S. Pat. No. 4,808,529; U.S. Pat. No. 5,116,729; U.S. Pat. No. 5,264,348; U.S. Pat. No. 5,620,863; and U.S. 2003/0077702 A1. These patents/patent application teach a method in which glucose is oxidized to gluconic acid with the release of hydrogen peroxide. The hydrogen peroxide is said to oxidize an indicator in the presence of a peroxidase to produce a measurable color, indicating the glucose content of the blood sample. Some recent patents suggest a process in which the glucose is converted first to gluconic acid and then to gluconolactone with the release of hydrogen peroxide. It has also been suggested that the gluconolactone is formed first and then hydrolyzed to gluconic acid. Regardless of which process scheme is correct, glucose oxidase enzymes have been used widely in dry strips and in other techniques for measuring the glucose contact of blood.

Various indicators have been employed in glucose sensors, such as benzidine-type indicators and heterocyclic azines. For example, 3,3',5,5'-tetramethylbenzidine and syringaldazine, luminol, o-tolidine, o-dianisitine, among others. One family of indicators is that of tetrazolium dye precursors. Examples of patents describing such indicators include U.S. Pat. No. 5,126,275, U.S. Pat. No. 5,322,680, U.S. Pat. No. 5,300,637, U.S. Pat. No. 5,290,536, U.S. Pat. No. 5,360,595 and U.S. Pat. No. 6,586,199. Tetrazolium indicators are used in the invention to be described below.

Of particular interest with regard to the present invention is the method described in U.S. Pat. No. 6,200,773 and its parent U.S. Pat. No. 5,902,731. In these patents, a test of the glucose content of blood employs glucose dehydrogenase (GDH), with NAD or PQQ or their derivatives, as a cofactor, a tetrazolium dye precursor, a diaphorase enzyme or an analog, and a nitrite salt. FIG. 5 of the '773 patent is a diagram of the process by which glucose is detected by development of color from the reduction of the tetrazolium dye precursor to a formazan.

PQQ (pyrroloquinoline quinone or its derivatives or isomers) as a cofactor for glucose dehydrogenase (GDH) enzymes has been of recent interest, as is evident from the disclosures in U.S. 2002/0076751 A1; EP 1 167 519 A1; U.S. Pat. No. 6,103,509; and JP 11243949 A2. In general, these disclosures teach the genetic modification of glucose dehydrogenase enzymes that are said to provide improved performance in glucose sensors.

The present inventors unexpectedly have found that a process similar to that discussed in U.S. Pat. No. 6,200,773 can be carried out in the absence of a mediator, such as the diaphorase enzyme. This finding makes possible a simpler method of detecting glucose in blood samples, as will be seen in the description of the invention below.

SUMMARY OF THE INVENTION

It has been discovered that certain glucose dehydrogenase—co-factor combinations can be used to provide a colorimetric response from tetrazolium indicators when they are in contact with glucose solutions but, without including the mediator that is normally required. In particular, PQQ dependent glucose dehydrogenase (PQQ-GDH) has been demonstrated to provide similar response to glucose, both with and without a mediator. Other quinone-dependent dehydrogenase enzymes are expected to provide similar performance with their corresponding donor compounds.

In one aspect, the invention is a reagent solution for measuring the concentration of glucose in blood. A glucose dehydrogenase (GDH) dependent on pyrroloquinoline quinone (PQQ) (or its derivatives or isomers) as a co-factor is used with a tetrazolium dye precursor, but without including a mediator such as PMS (phenazine methosulfate) or a diaphorase.

In another aspect, the invention is a dry test strip containing a GDH, PQQ (or a derivative or isomer) as a co-factor, and a tetrazolium dye precursor, but lacking the usual mediator. The strip will be contacted with glucose-containing blood and the developed color measured and correlated with the glucose content.

The invention also is an improved method of measuring the glucose content of whole blood using the test strips contain-

DESCRIPTION OF THE PREFERRED EMBODIMENTS

Measuring Glucose in Blood

Figure 1:
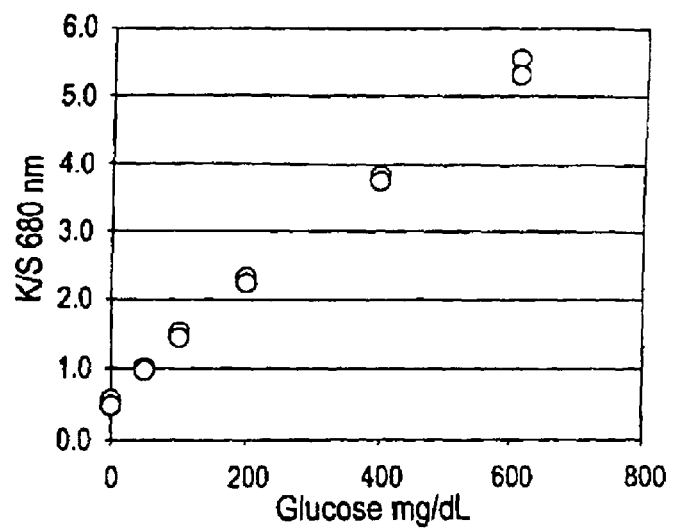
FIG. 1 is a graph of the results of Example 1.

In the methods which employ glucose oxidase, those enzymes are reacted with glucose, producing oxidized glucose and hydrogen peroxide. The hydrogen peroxide oxidizes an indicator compound in the presence of a peroxidase. The oxidized indicator produces a color that is correlated with the glucose content of the blood sample.

In the present invention, a glucose dehydrogenase is used, along with a co-factor and a tetrazolium dye precursor to produce a colored response proportional to the glucose content of the sample. Such reactions are normally described by the following sequence of reactions:

Glucose+GDH-co-factor$_{oxid}$→Gluconolactone+ GDH-co-factor$_{red}$

GDH-co-factor$_{red}$+Mediator$_{oxid}$→GDH-co-factor$_{oxid}$+ Mediator$_{red}$ Mediator$_{red}$+tetrazolium indicator→Mediator$_{oxid}$+ Formazan According to this sequence of reactions, glucose is converted to gluconolactone while the dehydrogenase-co-factor is reduced and then reoxidized by a mediator for further reaction with available glucose. The mediator may be any one of those familiar to those skilled in the art, such as PMS (phenazine methosulfate), PES (phenazine ethosulfate), DCIP (2,6,-dichlorophenolindophenol), and ferrocene. The mediator has been considered to be necessary to obtain a useful response by reducing the tetrazolium indicator to formazan. However, in the present invention, a mediator is not needed and a useful response is obtained in its absence, as will be shown in the examples below.

The inventors have found that the mediator is not required when the glucose dehydrogenase is classified as EC 1.1.99.17 (now EC1.1.5.2) (International Union of Biochemistry and Molecular Biology; Nomenclature and Classification of Enzyme-Catalyzed Reactions; NC-IUBMB). Such enzymes are dependent on certain co-factors, in this instance the co-factor is pyrroloquinoline quinone (PQQ) or derivatives or isomers thereof. Other glucose dehydrogenase enzymes are dependent on other co-enzymes or co-factors, such as nicotinamide adenine dinucleotide (NAD), flavin adenine dinueleotide (FAD), and their analogs. The reason for the successful use of PQQ-dependent GDH in the substantial absence of a mediator is not understood at this time. While not being bound by theory, it may be associated with the ability of the tetrazolium salt to come in more direct contact with the enzyme and/or its capacity to be less diffusion limited with respect to the co-factor.

Thus, in the method of the invention it appears that the tetrazolium indicator is reduced by the reduced dehydrogenase-co-factor according to the following reaction sequence:

Glucose+GDH-co-factor$_{oxid}$→Gluconolactone+ GDH-co-factor$_{red}$

GDH-co-factor$_{red}$+tetrazolium indicator→Formazan+ GDH-co-factor$_{oxid}$

Dehydrogenases

Glucose dehydrogenase enzymes are commercially available from Toyoba, Kyowa, Amano, Genzyme, Biozyme, among others and are either native enzymes or recombinant enzymes produced by classic fermentation and/or recombinant methods. In order to be effective, dehydrogenases require a co-factor, such as NAD, FAD and PQQ and their derivatives or isomers. Since the dehydrogenases have been obtained from their suppliers in combination with a co-factor they have been characterized by their suppliers and their nature is not fully known at this time. Combinations of dehydrogenase enzymes with known co-factors have been tested, with the results shown in the examples. As will be seen, PQQ-dependent GDH enzymes did not require the presence of a mediator.

The present inventors discovered that glucose dehydrogenase dependent on PQQ (or derivatives or isomers) did not require a mediator in order to measure reaction with glucose in the presence of a tetrazolium salt indicator. They believe that other dehydrogenase enzymes with quinones as acceptor (EC1.1.5 class) may behave similarly in oxidizing alcohols, or other CH—OH donor compounds.

Mediators

It has been considered necessary to include in a test system a mediator to reoxidize the reduced dehydrogenase-co-factor after the reaction with glucose to form the corresponding lactone. A diaphorase or PMS (phenazine methosulfate) are typical mediators. It is a feature of the present invention that a mediator is not needed. As will be shown in the examples below, the new reagent system will be seen to behave in a similar manner whether or not mediators are included.

Tetrazolium Indicators

Tetrazolium indicators are generally described in U.S. patents mentioned earlier. In U.S. Pat. No. 6,200,773 certain tetrazolium dye precursors are listed as being particularly useful in reactions with dehydrogenase-co-factor combinations. Among them is the tetrazolium compound designated WST-4, used in the examples below.

Examples 1

Detection of Glucose with Non-NAD-Dependent Glucose Dehydrogenase and WST-4

A strip of 0.8 μm polyethersulfone membrane was dipped in a solution containing 370 mM phosphate buffer, pH 7, 0.5% polymer (e.g. Teleostatin), surfactants (e.g., 0.1% Cremaphor EL and 0.2% Triton X305), 5.5 mg of Non-NAD (P)-dependent Glucose dehydrogenase [a quinone-dependent GDH designated EC 1.1.99.17 (now EC1.1.5.2)] from Toyobo, 800 U/mg, and 60 mM of indicator (WST-4 from Dojindo), but containing no mediator.

Glucose samples were prepared from 40% hematocrit whole blood samples and the concentration measured using the YSI glucose analyzer (Yellow Springs Instruments) as follows:
a) 0 mg/dL human plasma
b) 48 mg/dL human plasma
c) 101 mg/dL human plasma
d) 201 mg/dL human plasma
e) 397 mg/dL human plasma
f) 607 mg/dL human plasma When the reagent strip was contacted with glucose solutions a change in color developed that was proportional to the glucose concentration added. The color change was measured after 50-second development time by using a reflectance-measuring device. The reflectance was converted to K/S, a linearizing function developed from the Kubelka-Munk equations. K/S is equal to $(1-R^2)/2R$, where R is the measured reflectance. The response of each of two replicate glucose samples is shown in FIG. 1.

The results of Example 1 show that a measurable and substantially linear response was obtained even though no mediator (e.g., PMS) as described in the classic art of dehydrogenase based glucose sensors, was included in the reaction mixture.

Example 2

Comparison of Glucose Determination by Direct Detection to that of Classic Mediation A strip of polyethyleneterepthalate (PET, Melenex from Dupont) was coated with a mixture of buffer (0.25M phosphate, pH 7.4), and inactive ingredients (e.g., rheology modifying agents, opacifiers, and surfactants). In this example, a mixture included 0.6 g/L polyacrylate, 0.6 g/L polyvinyl alcohol, 1.5 g/L titanium dioxide, 1 g/L calcium carbonate, 0.001 to 0.006% of Silwet L-7600, Gerepon T-77, Surfonyl DF37, and containing 120 mM indicator (e.g., WST-4) and 6 KU/mL Non-NAD(P)-dependent Glucose Dehydrogenase (EC1.1.99.17, now EC1.1.5.2 from Bayer, patent pending). Another strip was coated with the same mixture to which 5 mM of mediator (PMS) was added. Whole blood plasma glucose samples were applied to samples of the above coated reagent and the change in color was measured as described in Example 1. Glucose samples were prepared from 40% hematocrit whole blood samples and the concentration of each measured using the YSI glucose analyzer (Yellow Springs Instruments) as follows:

a) 1 mg/dL human plasma
b) 56 mg/dL human plasma
c) 112 mg/dL human plasma
d) 224 mg/dL human plasma
e) 448 mg/dL human plasma
f) 678 mg/dL human plasma The mean reflectance of two replicates for each of the glucose samples was recorded at both 7 and 33 seconds after the sample was applied to the glucose reagent.

Figure 2:
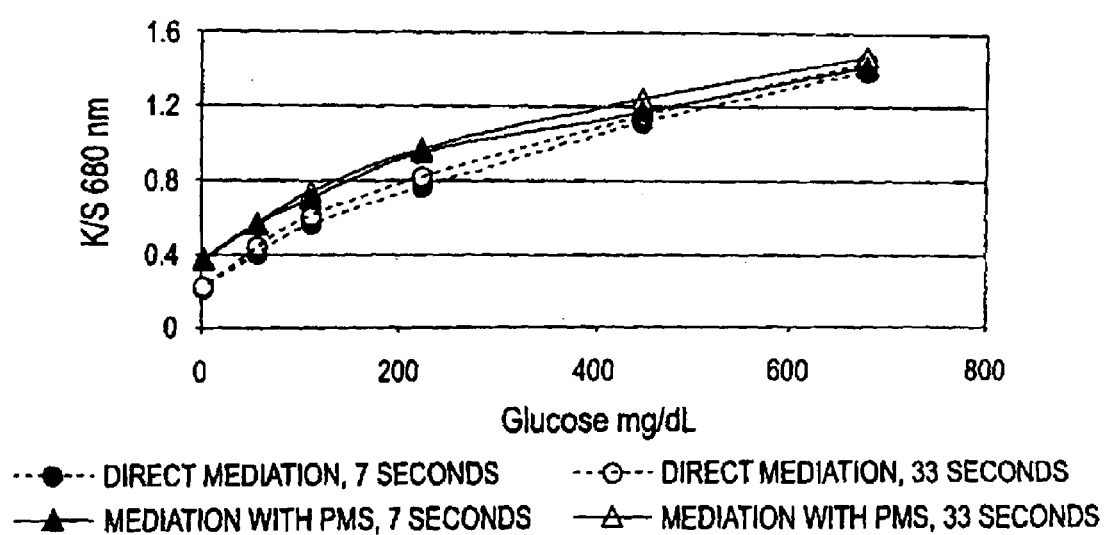
FIG. 2 is a graph of the results of Example 2.

The results of Example 2 (see FIG. 2) show that a measurable and substantially linear response was obtained with the direct mediation method and that the observed response was substantially the same as that of the classic mediation method. The speed of the detection was also demonstrated to be substantially the same as the classic detection method as is evidenced by the endpoint reflectance measured at test times of 7 seconds and 33 seconds.

Example 3

Example 2 was repeated except that a different tetrazolium salt indicator was used.

Figure 3:
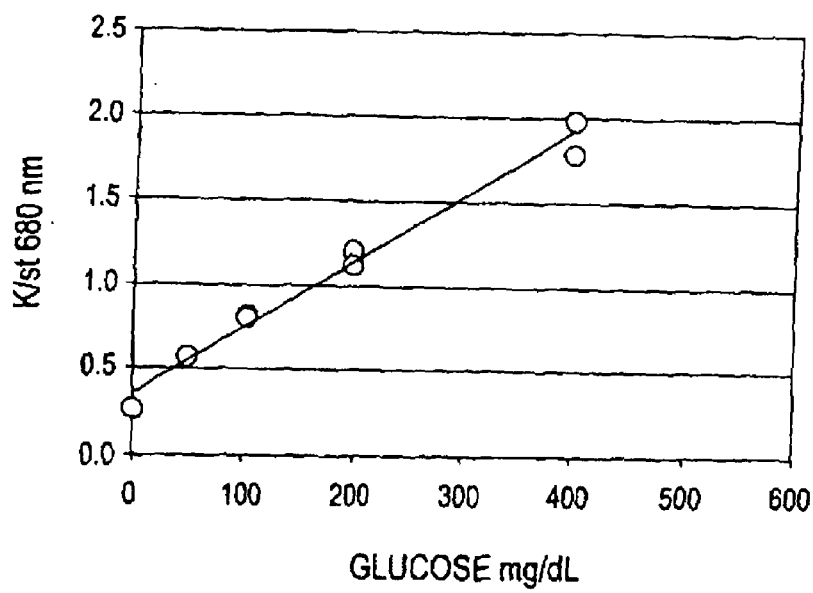
FIG. 3 is a graph of the results of Example 3.

Direct mediation with another tetrazolium salt was demonstrated by substituting an analog of HTC-45 (a thiazolyl tetrazolium salt of Bayer Corporation, see U.S. Pat. No. 5,126,275, column 21) for WST-4 in Example 1. After a 7 second reaction time, a substantially linear dose response to glucose was demonstrated, as can be seen in FIG. 3.

Example 4

Comparative

Figure 4:
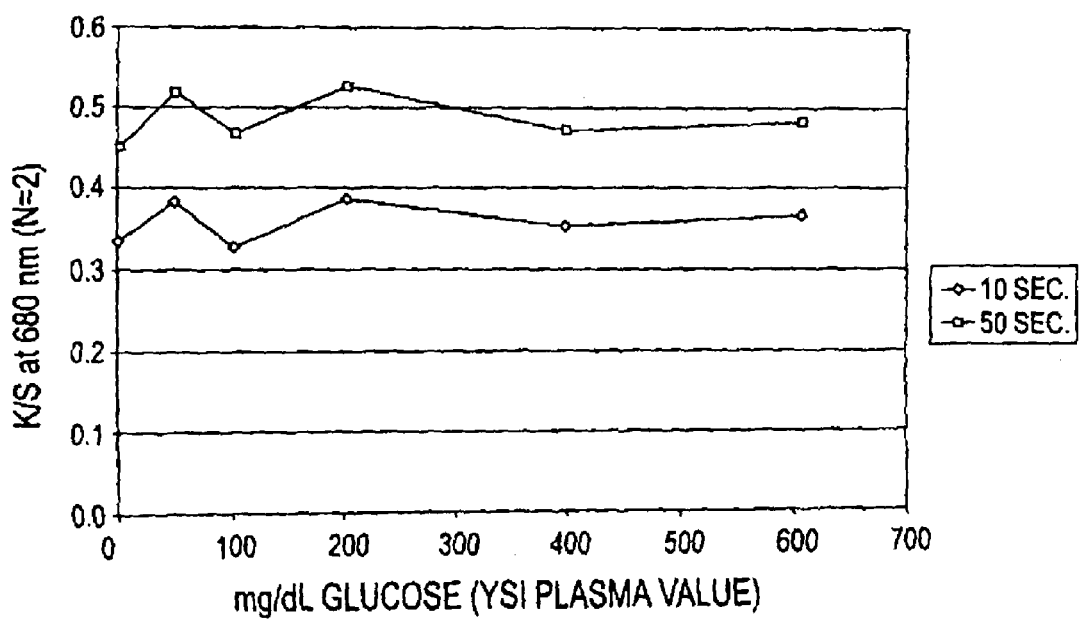
FIG. 4 is a graph of the results of Example 4.

A strip of 0.8 μm polyethersulfone membrane (Osmonics) was dipped in a solution containing NAD as a co-factor with NAD-dependent GDH (EC1.1.1.47) and a tetrazolium salt indicator, but without a mediator. The treated strip was contacted with glucose solutions having known concentrations. It was found that substantially no response was measured, as can be seen in FIG. 4.

Alternative Embodiment A

A reagent for measuring the concentration of glucose in blood comprising:
a) a glucose dehydrogenase (GDH);
b) as a co-factor for GDH, pyrrolo-quinoline quinone (PQQ) or a PQQ derivative or isomer, said GDH and co-factor being capable of reducing to a colored formazan a tetrazolium salt indicator in the substantial absence of a mediator; and
c) a tetrazolium salt indicator.

Alternative Embodiment B

A reagent of embodiment A wherein said glucose dehydrogenase of (a) is classified according to NC-IUBMB as EC1.1.99.17 (now EC1.1.5.2).

Alternative Embodiment C

A reagent of embodiment A wherein said co-factor is PQQ.

Alternative Embodiment D

A reagent of embodiment A wherein said co-factor is a PQQ derivative or isomer.

Alternative Embodiment E

At of embodiment A wherein said tetrazolium salt indicator is WST-4.

Alternative Embodiment F

A reagent of embodiment A wherein said tetrazolium salt indicator is an analog of HTC-45.

Alternative Embodiment G

A test strip for measuring the glucose in blood comprising:
(a) a support;
(b) a reagent layer disposed on said support, said reagent system comprising;
  (1) a glucose dehydrogenase (GDH);
  (2) as a co-factor for GDH, pyrrolo-quinoline quinone (PQQ) or a PQQ derivative or isomer, said GDH and co-factor being capable of reducing to a colored formazan a tetrazolium salt indicator in the substantial absence of a mediator; and
  (3) a tetrazolium salt indicator.

Alternative Embodiment H

A test strip of embodiment G wherein said glucose dehydrogenase of (b)(1) is classified according to NC-IUBMB as EC1.1.99.17 (now EC1.1.5.2).

Alternative Embodiment I

A test strip of embodiment G wherein said co-factor is PQQ.

Alternative Embodiment J

A test strip of embodiment G wherein said co-factor is a PQQ derivative or isomer.

Alternative Embodiment K

A test strip of embodiment G wherein said tetrazolium salt indicator is WST-4.

Alternative Embodiment L

A test strip of embodiment G wherein said tetrazolium salt indicator is an analog of HTC-45.

Alternative Embodiment M

A method for measuring glucose in blood comprising:
(a) a support;
(b) a reagent system disposed on said support, said reagent system comprising a glucose dehydrogenase (GDH), as a co-factor for GDH pyrrolo-quinoline quinono (PQQ) or a (PQQ) analog, said GDH and co-factor being capable of reducing a colored formazan a tetrazolium salt indicator in the absence of a mediator, and a tetrazolium salt indicator;
(c) measuring the color developed from said tetrazolium salt indicator; and
(d) correlating the color developed in step (b) with the glucose content of said blood sample.

Alternative Embodiment N

The method of embodiment M wherein said glucose dehydrogenase is classified as EC1.1.99.17.

Alternative Embodiment O

The method of embodiment M wherein said co-factor is PQQ.

Alternative Embodiment P

The method of embodiment M wherein said co-factor is a PQQ derivative or isomer.

Alternative Embodiment Q

The method of embodiment M wherein said tetrazolium salt indicator is WST-4.

Alternative Embodiment R

The method of embodiment M wherein said tetrazolium salt indicator is an analog of HTC-45.

While the invention is susceptible to various modifications and alternative forms, specific embodiments are shown by way of example in the drawings and are described in detail herein. It should be understood, however, that the invention is not intended to be limited to the particular forms disclosed. Rather, the invention is to cover all modifications, equivalents, and alternatives falling within the spirit and scope of the invention as defined by the appended claims.

The invention claimed is:

1. A reagent for measuring the concentration of glucose in blood comprising:
   (a) a glucose dehydrogenase (GDH);
   (b) as a co-factor for GDH, pyrrolo-quinoline quinone (PQQ) or a PQQ derivative or isomer, said GDH and co-factor being capable of reducing to a colored formazan a tetrazolium salt indicator in the absence of a separate mediator; and
   (c) a tetrazolium salt indicator.

2. A reagent of claim 1, wherein said glucose dehydrogenase of (a) is classified according to International Union of Biochemistry and Molecular Biology; Nomenclature and Classification of Enzyme-Catalyzed Reactions (i.e., NC-IUBMB) as EC1.1.99.17 (now EC1.1.5.2).

3. A reagent of claim 1, wherein said co-factor is PQQ.

4. A reagent of claim 1, wherein said co-factor is a PQQ derivative or isomer.

5. A reagent of claim 1, wherein said tetrazolium salt indicator is WST-4.

6. A reagent of claim 1, wherein said tetrazolium salt indicator is an analog of HTC-45.

7. A test strips for measuring the glucose in blood comprising:
   (a) a support;
   (b) a reagent layer disposed on said support, said reagent system comprising;
      (1) a glucose dehydrogenase (GDH);
      (2) as a co-factor for GDH, pyrrolo-quinoline quinone (PQQ) or a PQQ derivative or isomer, said GDH and co-factor being capable of reducing to a colored formazan a tetrazolium salt indicator in the absence of a separate mediator; and
      (3) a tetrazolium salt indicator.

8. A test strip of claim 7, wherein said glucose dehydrogenase of (b) (1) is classified according to NC-IUBMB as EC1.1.99.17 (now EC1.1.5.2).

9. A test strip of claim 7, wherein said co-factor is PQQ.

10. A test strip of claim 7, wherein said co-factor is a PQQ derivative or isomer.

11. A test strip of claim 7, wherein said tetrazolium salt indicator is WST-4.

12. A test strip of claim 7, wherein said tetrazolium salt indicator is an analog of HTC-45.

13. A method for measuring glucose in blood comprising:
    (a) a support;
    (b) a reagent system disposed on said support, said reagent system comprising a glucose dehydrogenase (GDH), as a co-factor for GDH pyrrolo-quinoline quinono (PQQ) or a (PQQ) analog, said GDH and co-factor being capable of reducing a colored formazan a tetrazolium salt indicator in the absence of a separate mediator, and a tetrazolium salt indicator;
    (c) measuring the color developed from said tetrazolium salt indicator; and
    (d) correlating the color developed in step (b) with the glucose content of said blood sample.

14. The method of claim 13, wherein said glucose dehydrogenase is classified as EC1.1.99.17.

15. The method of claim 13, wherein said co-factor is PQQ.

16. The method of claim 13, wherein said co-factor is a PQQ derivative or isomer.

17. The method of claim 13, wherein said tetrazolium salt indicator is WST-4.

18. The method of claim 13, wherein said tetrazolium salt indicator is an analog of HTC-45.

* * * * *